United States Patent
Onizuka et al.

(10) Patent No.: US 7,449,445 B2
(45) Date of Patent: Nov. 11, 2008

(54) CONDUCTIVE PEPTIDE NANOFIBER AND METHOD OF MANUFACTURE OF THE SAME

(75) Inventors: Kentaro Onizuka, Nara (JP); Shuhei Tanaka, Kobe (JP); Hirokazu Sugihara, Katano (JP); Atsuo Tamura, Kobe (JP)

(73) Assignees: Panasonic Corporation, Osaka (JP); National University Corporation Kobe University, Hyogo (JP)

( * ) Notice: Subject to any disclaimer, the term of this patent is extended or adjusted under 35 U.S.C. 154(b) by 433 days.

(21) Appl. No.: 11/252,719

(22) Filed: Oct. 19, 2005

(65) Prior Publication Data

US 2006/0089489 A1    Apr. 27, 2006

(30) Foreign Application Priority Data

Oct. 22, 2004    (JP) ............................. 2004-308542

(51) Int. Cl.
| | |
|---|---|
| *A61K 38/00* | (2006.01) |
| *A61K 51/00* | (2006.01) |
| *A61K 38/04* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *A61M 36/14* | (2006.01) |
| *A01N 37/18* | (2006.01) |

(52) U.S. Cl. .................... 514/2; 424/1.69; 530/345; 530/329; 530/333; 530/300; 930/280; 977/705; 977/729

(58) Field of Classification Search ................. 530/300
See application file for complete search history.

(56) References Cited

FOREIGN PATENT DOCUMENTS

JP    2005-146462    6/2005

OTHER PUBLICATIONS

Scheibel, Thomas., et al. "Conducting nanowires built by controlled self-assembly of amyloid fibers and selective metal deposition." PNAS, Apr. 15, 2003, vol. 100, No. 8, pp. 4527-4532 (also listed in the IDS of Dec. 22, 2005).*

Scheibel, Thomas., et al. "Conducting nanowires built by controlled self-assembly of amyloid fibers and selective metal deposition." PNAS, Apr. 15, 2003, vol. 100, No. 8, pp. 4527-4532.

* cited by examiner

*Primary Examiner*—Cecilia Tsang
*Assistant Examiner*—Maury Audet
(74) *Attorney, Agent, or Firm*—McDermott Will & Emery LLP

(57) ABSTRACT

A peptide nanofiber having conductivity is provided. A conductive peptide nanofiber which includes a nanofiber formed through a manner of self-assembly of a peptide that has a nanofiber-forming ability and consists of an amino acid sequence of Xaa-Phe-Ile-Val-Ile-Phe-Xaa (SEQ ID NO: 1, wherein N-terminal Xaa is an arbitrary amino acid residue $Xaa_1$; C-terminal Xaa is an arbitrary amino acid residue $Xaa_2$; and $Xaa_1$ and $Xaa_2$ are an amino acid having an acidic side chain, an amino acid having a basic side chain, or an amino acid having a side chain with polarity according as acidity and basicity) or a derivative of the peptide and a conductive substance added thereto, the aforementioned conductive substance being added to an amino group of the peptide or the derivative.

9 Claims, 11 Drawing Sheets

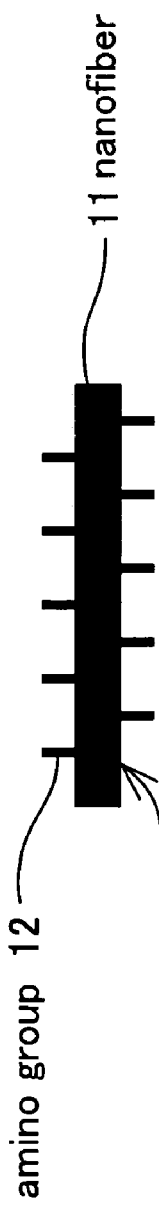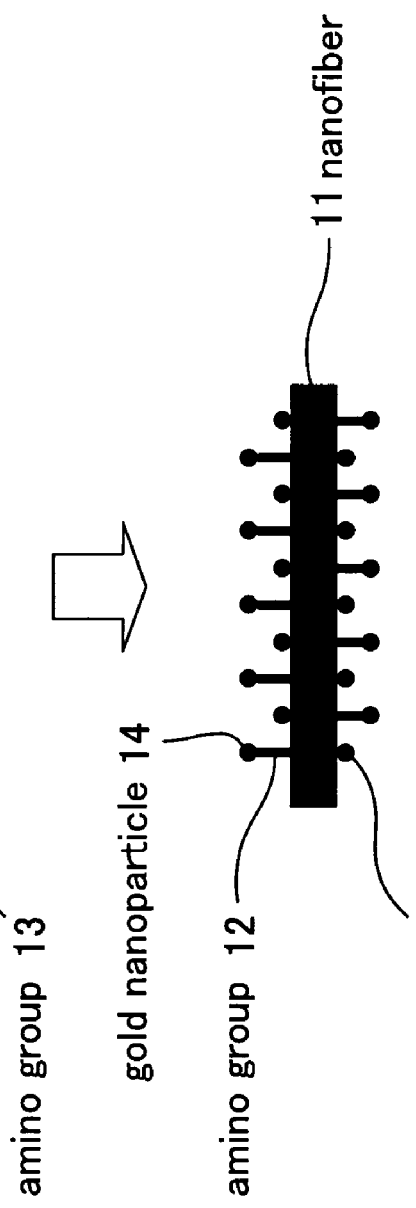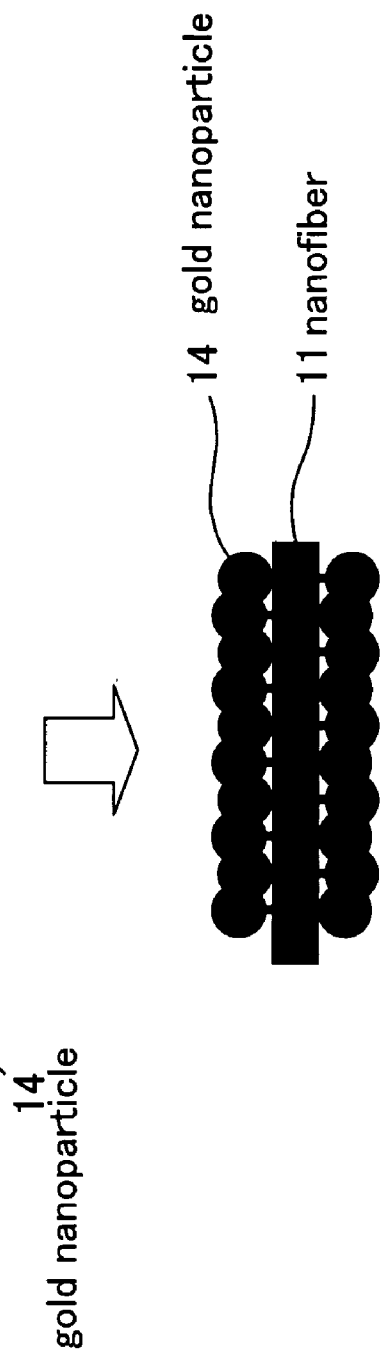

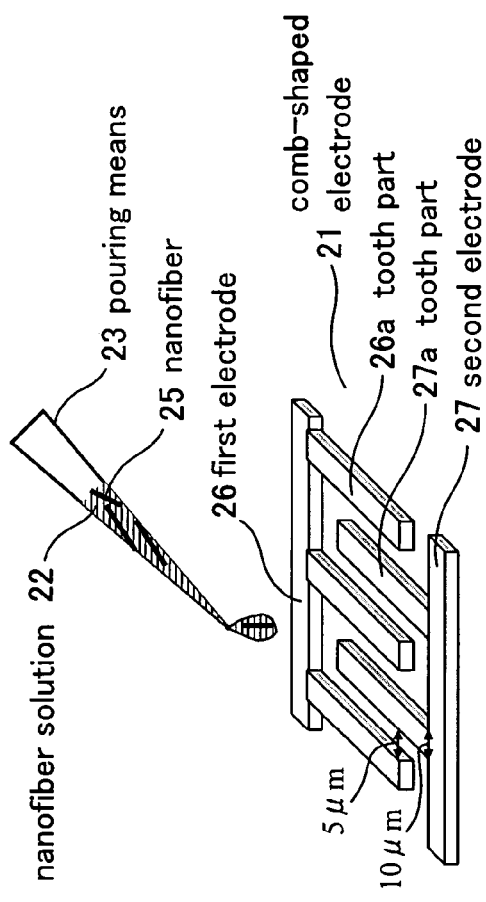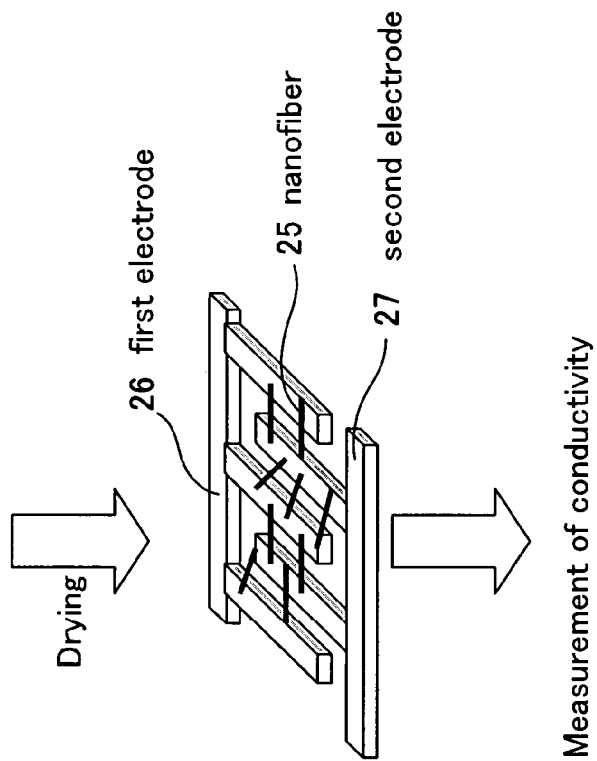
FIG.4A
FIG.4B

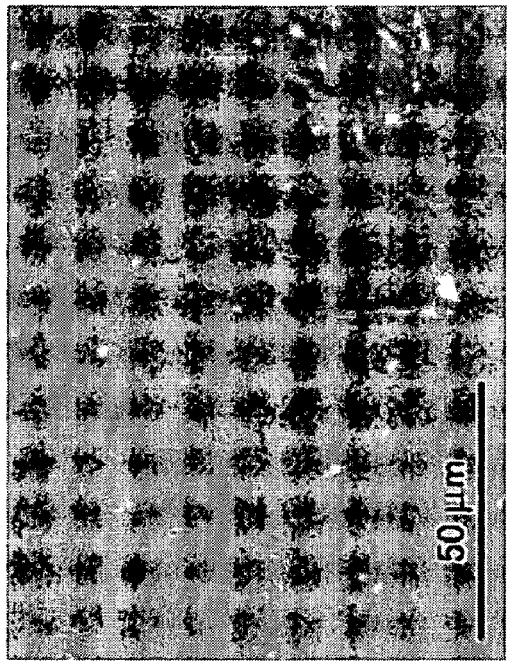
FIG.6B Microscopic image with differential interference
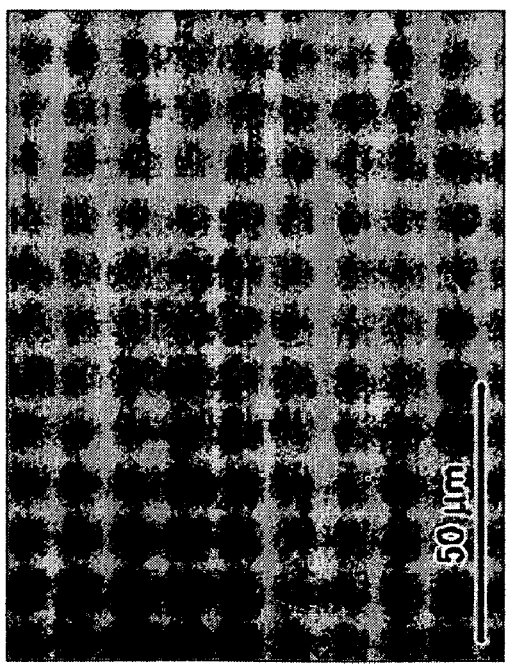
FIG.6A Microscopic image

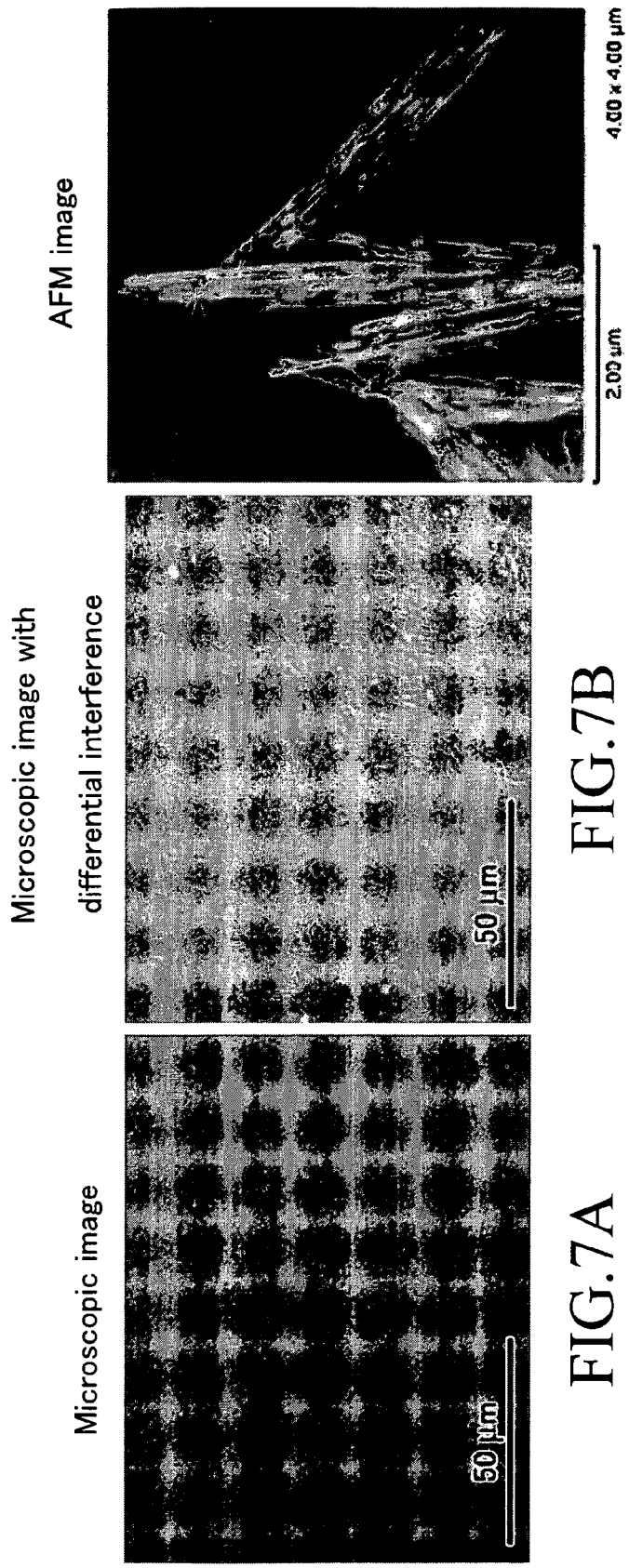
FIG.7A  Microscopic image
FIG.7B  Microscopic image with differential interference
FIG.7C  AFM image

CONDUCTIVE PEPTIDE NANOFIBER AND METHOD OF MANUFACTURE OF THE SAME

BACKGROUND OF THE INVENTION

1. Field of the Invention

The present invention relates to a peptide nanofiber having conductivity formed from a peptide that has a nanofiber-forming ability or a derivative of the peptide, and a method of manufacturing the same.

2. Description of the Related Art

Technology development for producing semiconductor elements and large-scale integrated circuits (LSI) using "top down" type approaches in which a large substance is subjected to miniaturization to give nanometer scale by cutting have been hitherto carried out extensively. However, such techniques have their limits, i.e., microstructures of 20 nm or less can not be produced. Thus, in recent years, investigations on construction of regular fine structures utilizing self-assembly of molecules have rapidly progressed. Representative examples of mimicking models for the "bottom up" type approach utilizing such self-assembly include cells of organisms, and investigations on development of novel materials with biomolecules using this as a model system have attracted great attention. Advantages of making a material with a biomolecule such as a protein or a nucleic acid constituting a living body involve the manufacturing system without waste because the material can be constructed through a manner of self-assembly without imparting energy externally, and bio-degradability of the substance per se, and the like. Thus, the material may be referred to as having least impact on the global environment and organisms. In particular, there exist 20 kinds of natural amino acids constituting proteins, and the formed structure as well as the function may vary diversely. Therefore, nanotechnologies utilizing proteins are believed to be important in various fields hereafter.

FIG. 1 shows a process of forming peptide bonds among amino acids to construct a chain structure, which forms a final tertiary structure spontaneously. As shown in FIG. 1, the protein that is a biopolymer has a chain structure (FIG. 1B) in which 20 kinds of amino acids (comparatively simple organic molecule) (FIG. 1A) are primarily bound by dehydrative condensation, and forms a complex tertiary structure (FIG. 1C) through folding thereof. Proteins are a substance which carries out a variety of functions in a living body, for example in human, approximately several tens of thousands kinds of proteins have been referred to be used. In addition, proteins have a comparatively regular secondary structure constructed by many residues on the sequence through a folding process. They have predominantly α-helical structures and β-sheet structures, including those in which almost tertiary structures are α-helical structures (α-proteins), those in which almost tertiary structures are β-sheet structures (β-proteins), mixtures of both of them (αβ-proteins) and the like. Accordingly, proteins have their inherent structure according to each amino acid sequence, and the tertiary structure determines the function of each protein.

In recent years, a phenomenon was found in which one or many kinds of proteins may denaturate from their original inherent structures to spontaneously aggregate into fibrous forms. Many of these are toxic in a living body, which are referred to as relating to diseases such as Alzheimer's disease, BSE (so called mad cow disease) and the like. Fibrous aggregates having a size in the level of nanometer formed by self-assembly of such a protein or a peptide are referred to as amyloid fiber. FIG. 2 is a schematic view illustrating the overview of formation of the amyloid fiber. In phenomena of aggregation of multiple proteins to give a fibrous form, parts forming the fiber take β-sheet structure in many cases. Even though they are proteins not originally having a β-sheet structure, the part involving in fiber formation takes a β-sheet structure. Consequently, as shown in FIG. 2A and FIG. 2B, it has been believed that a number of β-sheets are linked via a hydrogen bond between the molecules to form a fiber, thereby providing a characteristic structure in amyloid fibers. Amyloid fibers have been believed to take an extremely regular structure in a nanometer scale. However, despite of thus resulting expectation to technical or industrial utilization, such techniques have not been established yet under current circumstances.

Many of amyloid fibers that are generally formed are very stable, and are not disrupted even in a high temperature condition (approximately 100° C.). Such stability is believed to result from the hydrogen bond formed upon generation of fibrous form from the amyloid fiber, because the hydrogen bond is isolated from surrounding aqueous solution by aggregation of the fibers to give a state in which the hydrogen bond is hardly broken by a water molecule. Heretofore, investigations of amyloid fibers have been carried out in connection with diseases such as Alzheimer's disease and BSE. However, taking into account of technical aspects, the factor, i.e., a stable fibrous structure, is believed to be an important property when various processings are performed while keeping the fibrous shape. Also, amyloid fibers have a diameter of approximately several nanometers, and a length may reach to several hundred nanometers to several ten micrometers, as the case may be. Therefore, they can be utilized as a nanofiber. Additionally, for making nanofibers have a greater deal of utility value, the nanofiber may be endowed with any function.

As described hereinabove, nanofibers are believed to take a structure with β-sheets linked in conjunction, suggesting availability as ultra-precise structural materials controlled at the nanoscale level. Arrangement of functional molecules is enabled while controlling at the nano level, thereby capable of providing materials that contribute to important technologies in technical and industrial aspects.

Further, because the structure of the amyloid fiber that is one of nanofibers is very stable, a greater deal of utility value as a structural material is suggested. Also, because of its biodegradability, it can be a material that is favorable for the environment. Therefore, when functional nanofibers can be produced through imparting a function to such a nanofiber, applications thereof in various fields are expected. In trends of recent semiconductor process technologies viewed as one example of the field of their application, much smaller width of wiring between the functional elements in a semiconductor device has been demanded. Under such circumstances, techniques for wiring using a nanofiber have been also attracted attention. Hence, organic molecules and the like having conductivity have focused interest. Scheibel, T., Parthasarathy, R., Sawicki, G., Lin, X. M., Jaeger, H., Lindquist, S. L., Proc. Natl. Acad. Sci. USA, 100, 4527-4532 (2003) reports an example in which a conductive function was imparted using a pathogenic protein that forms amyloid fibers, followed by binding of gold particle to the formed fiber. In this report, a conductive function is imparted by substituting one residue in a giant pathogenic protein comprising 253 residues with Cys, binding a gold particle to the Cys, subjecting to silver plating, and then subjecting to gold plating.

SUMMARY OF THE INVENTION

The conductive amyloid fiber formed by the method described in Scheibel, T., et al., Proc. Natl. Acad. Sci. USA, 100, 4527-4532 (2003) was obtained by aggregation of the giant protein with a β-sheet structure, however, it is not clear as to which region on the sequence forms the β-sheet structure. Therefore, addition of functional molecules at a desired three-dimensional position may be difficult, thus resulting in difficulty in designing for the purpose of imparting a desired property. In turn, to obtain nanofibers having a desired property is still difficult. Alternatively, in order to impart desired conductivity, metal plating must be conducted as often as twice. Furthermore, in proteins having Cys, there is a risk of formation of a disulfide bond between Cys unless the protein is especially kept in the solution in a reduced state.

Use of a short peptide having only a portion required for fiber formation, as a conductive nanofiber, is more advantageous than use of a giant protein in terms of technical utilization. One ground of the advantage is exponentially inferior efficiency of synthesis as well as longer time period required for the synthesis, as the sequence becomes longer in the synthesis according to a current method of solid phase peptide synthesis using an Fmoc method or the like. Accordingly, taking into account of industrial development eventually, smaller number of residues of the peptide is more advantageous in terms of efficiency of the synthesis and synthesis time.

Further, the second ground for the advantage is ease of purification and separation of the synthesized peptide. As the number of the constituting amino acid residues is larger, the amount of byproduct having a molecular weight approximate to the intended peptide would be also greater, thereby causing difficulties in purification and separation. To the contrary, as the peptide is shorter, less by product is yielded, thereby enabling easy purification and separation. In addition, the peptide nanofiber has a structure that may be comparatively easily predicted, therefore, it can be readily designed so that desired properties are achieved. Moreover, when gold particles were bound thereto, the distance among the gold particles shall be so short that conductivity can be imparted by metal plating conducted just once. Thus, problems in conductive nanofibers produced using a giant protein as described above will be solved. Further, use of a peptide as a nanofiber may be advantageous in many aspects such as significant homogeneity of the formed nanofiber shape, high velocity of nanofiber formation, and the like.

An object of the present invention is to provide a conductive peptide nanofiber having conductivity imparted thereto without utilizing Cys in the amino acid sequence. There are two following problems for accomplishing the aforementioned object. a) How conductivity should be imparted to a peptide nanofiber; and b) What is the peptide sequence having a stable fiber-forming ability without inhibition of nanofiber formation resulting from a processing for imparting the conductivity, and without destruction of thus formed nanofiber.

In order to accomplish the aforementioned object, the present invention provides the followings.

(1) A conductive peptide nanofiber which comprises a nanofiber formed through a manner of self-assembly of a peptide that has a nanofiber-forming ability and consists of an amino acid sequence of Xaa-Phe-Ile-Val-Ile-Phe-Xaa (SEQ ID NO: 1, wherein N-terminal Xaa is an arbitrary amino acid residue $Xaa_1$; C-terminal Xaa is an arbitrary amino acid residue $Xaa_2$; and $Xaa_1$ and $Xaa_2$ are an amino acid having an acidic side chain, an amino acid having a basic side chain, or an amino acid having a side chain with polarity according as acidity and basicity) or a derivative of the peptide, and a conductive substance added thereto, the conductive substance being added to an amino group of the peptide or the derivative. In above (1), conductivity can be imparted by adding a conductive substance to an amino group, thereby solving the aforementioned Problem a). Furthermore, in above (1), the "nanofiber formed through a manner of self-assembly of a peptide or a derivative of the peptide" includes nanofibers formed through a manner of self-assembly of a salt of the peptide or a salt of the derivative. Use of a peptide having an amino acid sequence set out in SEQ ID NO: 1, the derivative, or a salt thereof upon formation of the nanofiber achieves stable fiber-forming ability, which fiber-forming ability can be further retained also in the treatment for imparting conductivity, or the formed fiber can be prevented from destruction, thereby solving the aforementioned problem b).

(2) The conductive peptide nanofiber according to (1) wherein $Xaa_1$ and $Xaa_2$ are a amino acid selected from the group consisting of Asp, Glu, Arg, Lys, His, Asn, and Gln.

(3) The conductive peptide nanofiber according to (2) wherein the amino group is an N-terminal amino group.

(4) The conductive peptide nanofiber according to (2) wherein at least one of $Xaa_1$ and $Xaa_2$ is Lys, and the amino group is an amino group at side chain end of Lys.

(5) The conductive peptide nanofiber according to (2) wherein $Xaa_1$, is Glu, and $Xaa_2$ is Lys.

(6) The conductive peptide nanofiber according to (2) wherein the conductive substance is a gold particle.

(7) The conductive peptide nanofiber according to (6) wherein the gold particle has a diameter of 1 nm or greater and 20 nm or less.

(8) The conductive peptide nanofiber according to (6) wherein the gold particle is covered by a metal formed by allowing a metal ion to deposit, with the gold particle as a core.

(9) The conductive peptide nanofiber according to (8) wherein the metal ion is a gold ion or a silver ion.

(10) The conductive peptide nanofiber according to (1) wherein the conductive substance is added to an amino group of the peptide or the derivative of the peptide via an amino group-reactive material.

(11) A method of manufacturing a conductive peptide nanofiber comprising: (a) preparing a nanofiber formed through a manner of self-assembly of a peptide that has a nanofiber-forming ability and consists of an amino acid sequence of Xaa-Phe-Ile-Val-Ile-Phe-Xaa (SEQ ID NO: 1, wherein N-terminal Xaa is an arbitrary amino acid residue $Xaa_1$; C-terminal Xaa is an arbitrary amino acid residue $Xaa_2$; and $Xaa_1$ and $Xaa_2$ are an amino acid having an acidic side chain, an amino acid having a basic side chain, or an amino acid having a side chain with polarity according as acidity and basicity), or a derivative of the peptide; and (b) adding a conductive substance to an amino group of the peptide or the derivative following the step (a).

(12) The method of manufacturing a conductive peptide nanofiber according to (11) wherein the conductive substance is a gold particle.

(13) The method of manufacturing a conductive peptide nanofiber according to (12) which further comprises (c) allowing a metal ion to deposit, with the gold particle as a core following the step (b).

BRIEF DESCRIPTION OF THE DRAWINGS

FIG. 3 is a cross sectional view schematically illustrating one example of a method of manufacturing a conductive nanofiber.

FIG. 4 is a view schematically illustrating steps of measuring conductivity.

FIG. 6A shows a light microscopic image of a nanofiber of EK7aa, and FIG. 6B shows a light microscopic image obtained by observation with a differential interference filter.

FIG. 7A shows a light microscopic image of a nanofiber of EK7aa to which gold particles were added, FIG. 7B shows a light microscopic image obtained by observation with a differential interference filter, and FIG. 7C shows an AFM image.

DETAILED DESCRIPTION OF THE INVENTION

Figure 1A:
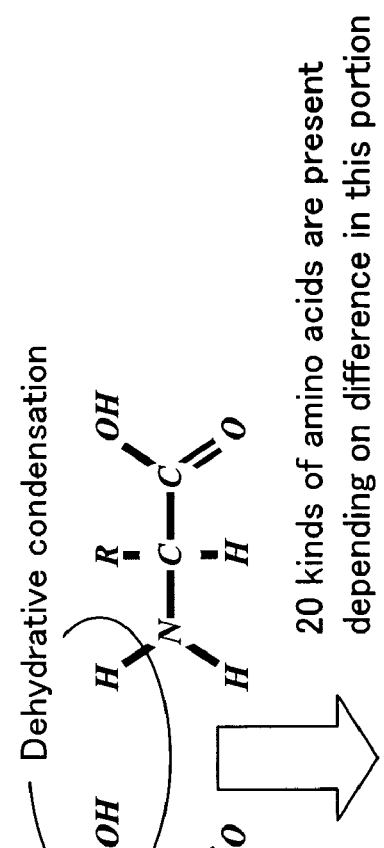
FIG. 1 is a view illustrating a process of peptide bonding of amino acids, and formation of a final tertiary structure.
Figure 1B:
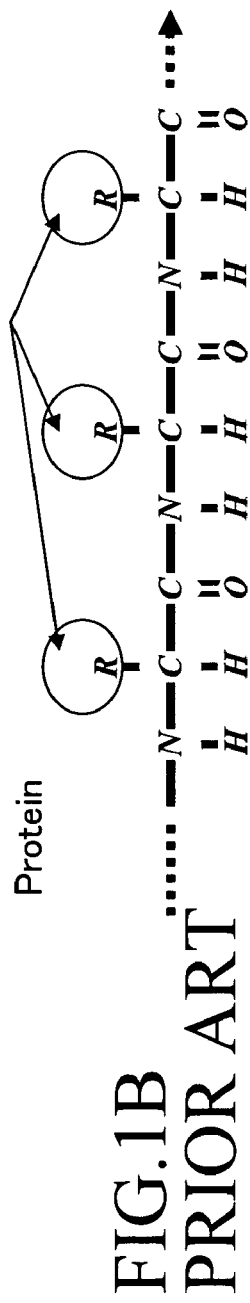
Figure 1C:
Figures 2A, 2B:
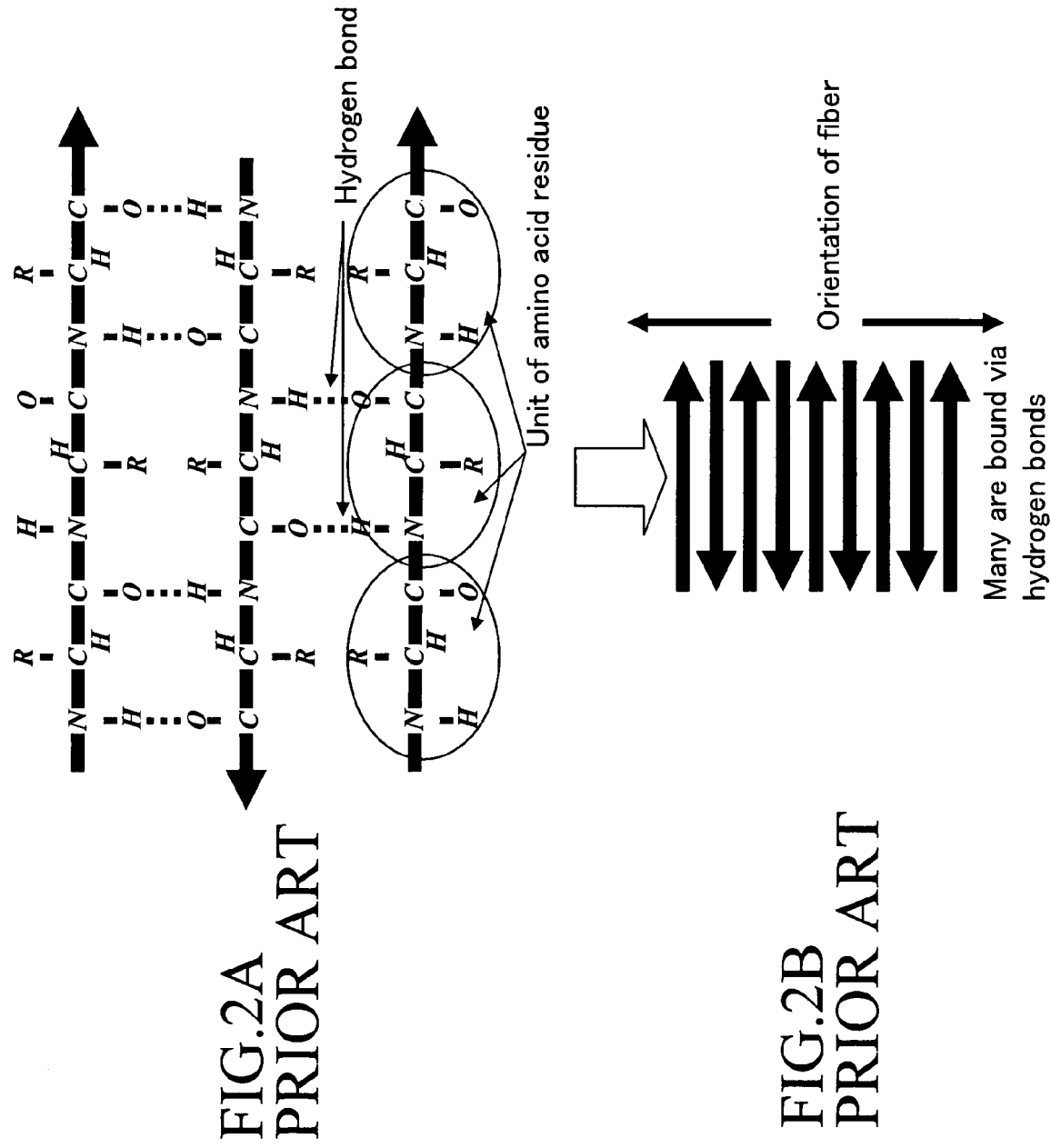
FIG. 2 is a schematic view illustrating an overview of formation of an amyloid fiber.

The present invention provides a conductive nanofiber using a short peptide of 7 residues efficiency of industrial production of which is superior, and provides one possible conductive wiring member in the field requiring fine wiring. In addition, because a short peptide is used, three-dimensional structure can be readily predicted, and designing for attaining a desired property will be easy. In the present invention, a conductive substance can be added without using Cys, therefore, a conductive peptide nanofiber can be manufactured even in a solution except for one in the reduced state.

The peptide nanofiber can be also prepared utilizing an organism, thus no adverse influence on the environment is exerted. Furthermore, because of biodegradability, a nanofiber that is favorable for the environment may be provided also in this respect.

PREFERRED EMBODIMENTS OF THE INVENTION

Hereinafter, the peptide of the present invention will be explained in more detail with reference to embodiments and Examples, but the present invention is not limited thereto.

The present invention relates to a conductive peptide nanofiber which comprises a nanofiber formed through a manner of self-assembly of a peptide that has a nanofiber-forming ability and consists of an amino acid sequence of Xaa-Phe-Ile-Val-Ile-Phe-Xaa (SEQ ID NO: 1, wherein N-terminal Xaa is an arbitrary amino acid residue $Xaa_1$; C-terminal Xaa is an arbitrary amino acid residue $Xaa_2$; and $Xaa_1$ and $Xaa_2$ are an amino acid having an acidic side chain, an amino acid having a basic side chain, or an amino acid having a side chain with polarity according as acidity and basicity) or a derivative of the peptide, and a conductive substance added thereto. The aforementioned conductive substance is added to an amino group of the peptide or a derivative of the peptide. There is a possibility that the peptide or the derivative of the peptide has an N-terminal amino group, an amino group of the side chain of the amino acid residue, or an amino group of the functional group bound to the peptide in case of the derivative of the peptide. To such an amino group can be added the aforementioned conductive substance. The $Xaa_1$ and $Xaa_2$ may be, in case of natural amino acids, Asp or Glu having an acidic side chain, Arg, Lys or His having a basic side chain, or Asn or Gln having a side chain with polarity according as acidity or basicity.

Examples of the conductive substance include molecules having a π electron such as molecules having a phenyl group, metal particles and the like. The conductive substance is added to an amino group of the peptide or the derivative of the peptide via, for example, an amino group-reactive material. One Example of the amino group-reactive material includes sulf-N-hydroxy succinimide. On the grounds that gold particles to which this material is added are readily available and the like, the conductive substance which may be preferably used is a gold particle.

It is preferred that a metal particle is added to the amino group of the peptide or the peptide derivative because covering with the metal particles by allowing a metal ion to deposit using the metal particle as a core facilitates the metal added to different amino groups to be brought into contact with each other, thereby allowing easy securement of the conductivity.

For example, when gold nanoparticles were added to an amino group of a peptide or a peptide derivative, conductivity can not be secured unless the gold nanoparticles are in contact with each other. In such cases, a process for allowing a silver ion or a gold ion to deposit around the gold nanoparticle so that the gold nanoparticles are in contact with each other. When gold plating or silver plating is executed, gold nanoparticles must be immobilized on the nanofiber because metal plating is not perfected unless a metal to be a core is not added to the sample to be subjected to plating.

FIG. 3 is a cross sectional view schematically illustrating one example of a method of manufacturing a conductive nanofiber. First, a nanofiber 11 consisting of a peptide of Glu-Phe-Ile-Val-Ile-Phe-Lys (SEQ ID NO: 2) is provided (FIG. 3A). Next, gold nanoparticles 14 having a diameter of 1.4 nm are added to amino groups 12, 13 of the peptide. Because an N-terminal amino group 13 and an amino group 12 of the Lys residue are present within the peptide, gold nanoparticles 14 are added to these amino groups 12, 13 (FIG. 3B). The gold nanoparticle which may be used has a diameter of preferably 1 nm or greater and 20 nm or less, and more preferably 1 nm or greater and 5 nm or less. Although large gold nanoparticles (for example, having a diameter of 10 nm or greater) may be also used from the beginning, the amino group of the peptide and the gold nanoparticle may be much less likely to bind in this instance. Thus, higher conductivity can be imparted by adding smaller gold nanoparticles (for example, having a diameter of 1 nm or greater and 5 nm or less) first, and then enlarging them by way of deposition of a gold ion.

Next, a gold ion is allowed to deposit around the gold nanoparticle 14 as a core, thereby covering the gold nanoparticle 14 with thus deposited gold (FIG. 3C). According to this step, gold nanoparticles 14 are brought into contact with each other to manufacture a conductive peptide nanofiber. In FIG. 3, the overview of addition of the gold nanoparticles to all amino groups of the peptide is shown, which is a schematic example. However, practically, the gold particles may not be added to all the amino groups. Even in such cases, contact of multiple peptide nanofibers 11 with each other, enlargement of the gold nanoparticles, or the like enables manufacture of a peptide nanofiber having conductivity.

In the above method of manufacture, a short peptide of 7 residues was used. Use of such a short peptide allows gold nanoparticles on the nanofiber to be brought into close contact with each other, thereby also enabling imparting a conductive function by metal plating once. Thus, the step of imparting conductivity may involve less waste, and can be carried out efficiently.

The "derivative of the peptide" referred to herein means a peptide to which a functional group is covalently bound to a main chain and/or a side chain of the amino acid constituting the peptide. Examples of the derivative of the peptide include those to which a methyl group, an acetyl group, a phosphoric acid group or a formamide group covalently bound to the main chain and/or a side chain of the peptide.

Examples of the salt of the peptide or the salt of the derivative of the peptide include sodium salts, potassium salts, phosphate, acetate, hydrochloride and the like.

The peptide may be either prepared by chemical synthesis using a liquid phase system or a solid phase system, or prepared by expression in *Escherichia coli* using a cDNA encoding the intended sequence followed by purification. The cDNA which may be used in this process may be prepared by common chemical synthesis.

EXAMPLES

In this Example, the amino acid sequence of a peptide nanofiber to which a conductive function was imparted is Glu-Phe-Ile-Val-Ile-Phe-Lys (SEQ ID NO: 2), the abbreviation of which herein being EK7aa.

(Experimental Method)

1. Synthesis of Peptide

Synthesis of peptide was conducted based on solid phase synthesis with a peptide synthesis system (Pioneer; Applied Biosystems). Support resin used in the solid phase synthesis was a PEG-PS resin (Applied Biosystems) to which: a 9-fluorenylmethoxycarbonyl (Fmoc) protecting group was added for protecting the $N_\alpha$-amino group; a t-butoxycarbonyl (tBoc) protecting group was added for protecting the lysine residue side chain; and a t-butoxy (OtBu) protecting group was added for protecting the glutamic acid side chain. For coupling of the amino acid, an amino acid to which the protecting group was introduced (Peptide Institute, Inc.) was used, while N-[(dimethylamino)-1H-1,2,3-triazole[4,5-6]pyridin-1-ylmet hylene]-N-methylmethanaminium hexafluorophosphate N-oxide (HATU) (Applied Biosystems) was used as a coupling reagent. Deprotecting reaction of the peptide protecting group was carried out in the mixed solution (0.5 ml purified water, 9.5 ml TFA) over 1.5 to 2 hrs at room temperature. Thereafter, thus deprotected peptide was extracted with t-butyl methyl ether (MTBE). After recovery by centrifugation, the peptide was obtained by drying in a vacuum.

Purification of the peptide was performed using a Develosil ODS column (Nomura Chemical) on reverse-phase high-pressure liquid chromatography (RP-HPLC) (Hitachi, Ltd.). The chromatography was conducted at a flow rate of 10 ml/min, with gradient in elution by altering the concentration of the eluent B from 20% to 50% over 30 min. The eluent A employed was purified water (0.1% TFA), while the eluent B was acetonitrile (0.1% TFA). The peptide purified on HPLC was ascertained using a matrix-assisted laser desorption ionization; MALDI process with a time-of-flight mass spectrometer (AXIMA-CFR, Shimadzu Corporation).

2. Nanofiber Forming Reaction

The peptide was weighed, which was dissolved in 90% aqueous methanol solution to give a 3 mM peptide stock solution. Further, a phosphate buffer solution (pH 7.5) was prepared. Then, an aliquot from the peptide stock solution was taken and diluted in the phosphate buffer solution so that the peptide concentration became 300 μM (9% methanol, 25 mM phosphate buffer solution, pH 7.5). Accordingly, the fiber forming reaction was initiated.

3. Atomic Force Microscopic (AFM) Observation

An aliquot of 2 μl was taken from each sample, dropped onto a mica substrate (about 1 cm square), and left to stand at room temperature for 1 to 5 min. Thereafter, for washing the substrate, 50 μl of purified water was dropped from the top of the tilted substrate using a micro pipette. After repeating this procedure twice, it was completely dried at room temperature. Then, AFM (SPM-9500J2, Shimadzu Corporation) observation was conducted.

4. Circular Dichroism (CD) Spectrometry

An aliquot of about 200 μl of the peptide solution was taken, and was placed in a cylinder type quartz cell having a light path length of 0.1 cm to measure CD in far-ultraviolet region of 250 nm to 190 nm (Jasco J-720 spectropolarimeter, JASCO Inc.).

5. Light Microscopic Observation (1) Congo Red (CR) Binding Assay

After adding a 80% aqueous methanol solution to weighed CR (Nacalai Tesque, Inc.), the solution was suspended by vortexing, and the block of residual CR was pulverized by sonication over 1 min. After centrifugation (15000 rpm) for 10 min, the supernatant solution was passed through a filter having a pore size of 0.45 μm (Sartorius) twice to produce a CR-saturated solution. After dropping 10 μl of the sample on a slide glass (Matsunami Glass Ind., Ltd.) and dried once, 10 μl of the previously prepared CR-saturated solution was dropped on the dried sample, and dried again. Thus produced sample was observed using a polarizing microscope (Nikon ECLIPSE E600 POL, Nikon Corporation).

(2) Bright Field Observation

An aliquot of the sample of 5 to 10 μl was taken, placed on a slide glass, and dried. Thereafter, bright field observation was conducted using a light microscopy (Nikon ECLIPSE E600 POL, Nikon Corporation). Similar observation was conducted with a differential interference filter (Nikon Corporation) only in case where the magnification was ×500.

6. Biotinylation of Nanofiber and Measurement of Biotinylation Efficiency

Biotinylating reagent used for biotinylation of the nanofiber is Biotin-$(AC_5)_2$ Sulfo-Osu (hereinafter, merely referred to as biotin) (DOJINDO Laboratories), which binds to a free amino group of the peptide (ε-amino group of a lysine residue or the like) as a binding site. This biotinylating reagent was added to the nanofiber to give 10 times the peptide concentration (300 μM), and the mixture was shaken at 25° C. for 12 hrs. Thereafter, the entire solution was recovered, which was dialyzed for 18 hrs or longer to remove unreacted biotin (Spectra/Por membrane, MWCO: 3500).

In order to estimate efficiency of the biotinylation, 4-hydrooxyazobenzene-2-carboxylic acid (HABA) (Pierce) was weighed, and thereto was added a 10 mM aqueous NaOH solution to give 10 mM HABA (preparation of HABA solution). Further, avidin (Pierce) was weighed, and thereto were added phosphate buffered saline (PBS) and previously prepared HABA solution, thereby adjusting to give the final concentration of avidin of about 7 μM, and the final concentration of HABA of about 300 μM (preparation of HABA-avidin solution). The HABA-avidin solution in a volume of 180 μl was placed in a micro-cell (light path length: 1 cm), and absorbance at 500 nm was measured with an ultraviolet spectrophotometer (HITACHI U-3210 spectrophotometer). This procedure was repeated three times, and the average value of the three-time measurement was determined as the value intended (the value defined as $Abs_A$). Next, to 180 μl of the HABA-avidin solution was added 20 μl of the biotinylated fiber. After leaving the mixture to stand still for 5 min, absorbance at 500 nm was similarly measured (the value defined as $Abs_B$). Concentration of biotin immobilized on the fiber [A (mol/l)] was calculated from the values of $Abs_A$ and $Abs_B$, according to the following formula (1):

$$A(mol/l) = [10^4 \times (0.9 \times Abs_A - Abs_B)/34] \times 10^{-6} \quad \text{formula (1)}$$

When concentration of the biotinylated peptide is supposed to be B (mol/l), number of biotin that labelled one molecule of the peptide can be calculated by the following formula (2):

$$A/B = \text{number of biotin bound to one molecule of the peptide (mol/mol)}$$

7. Method of Imparting Conductive Function

Conductive function was imparted by allowing an amino group of the N-terminus or of the side chain of a lysine residue of the peptide, expected as being exposed on the surface of the formed nanofiber, to covalently bind to a gold nanoparticle to which sulf-N-hydroxy succinimide was added as a functional group (diameter 1.4 nm) (hereinafter, merely referred to as gold nanoparticle). In practice, an aliquot of 400 μl was taken from the nanofiber solution 2 days or more after formation of the nanofiber, and it was placed in a tube (Nanoprobes) in which freeze-dried gold nanoparticles had been charged. After agitation with brief vortexing, the mixture was stirred at a low temperature of 4° C. for 12 to 18 hrs with a rotor (Petit rotor MODEL 2210, Waken Yaku Co., Ltd.). Thereafter, the solution was entirely recovered, and dialyzed in order to remove unreacted gold nanoparticles for 18 hrs or longer (Spectra/Por membrane, MWCO: 10000). After recovering the nanofiber solution from the dialysis membrane, it was centrifuged at 4° C., 10000 rpm for 10 min. The supernatant solution was discarded, and thereto was added purified water again followed by centrifugation similarly. This operation of centrifugation was repeated 5 times.

(1) Silver Plating

To the aqueous nanofiber solution was added an equal volume of an LI Silver mixed solution. The reaction was allowed at room temperature for 20 min to execute silver plating of the gold nanoparticles on the nanofiber modified therewith. The LI Silver mixed solution had been prepared by mixing an LI Silver Initiator solution (Nanoprobes) with an LI Silver Enhancer solution (Nanoprobes) in a ratio of 1:1.

(2) Gold Plating

To the aqueous nanofiber solution was added an equal volume of a GoldEnhance LM mixed solution. The reaction was allowed at room temperature for 20 min to execute gold plating of the gold nanoparticles on the nanofiber modified therewith. The GoldEnhance LM mixed solution had been prepared by mixing a GoldEnhance LM solution A, B, C, and D in a ratio of 1:1:1:1.

After plating with each type, the mixture was centrifuged at 4° C., 10000 rpm for 10 min. The supernatant solution was discarded, and thereto was added purified water again followed by centrifugation similarly. This operation of centrifugation was repeated 5 times.

8. Measurement of Conductivity

FIG. 4 is a view schematically illustrating steps of measuring conductivity. For measurement of the conductivity, a comb-shaped electrode 21 (electrode width: 10 μm, electrode interval: 5 μm, electrode material: carbon) (manufactured by BAS Inc.) including a first electrode 26 having a tooth part 26a and a second electrode 27 having a tooth part 27a was used (see, FIG. 4A). First, as shown in FIG. 4A, a sample containing a nanofiber 25 of any one of the prepared EK7aa peptide nanofiber, the nanofiber to which the gold particles were added, the nanofiber subjected to silver plating, and the nanofiber subjected to gold plating was employed as a nanofiber solution 22. The nanofiber solution 22 in a volume of 0.5 μl was dropped using a pouring means 23 from above the comb-shaped electrode 21 to place on tooth parts 26a, 27a, and then dried as shown in FIG. 4B. Because the EK7aa peptide nanofiber includes phosphoric acid as the solvent, the electrode 21 was washed with 50 μl of purified water three times after the nanofiber solution 22 was placed and dried on the tooth parts 26a, 27a. Measurement of conductivity was carried out by determining direct-current electricity and impedance using HAG-1510 m manufactured by Hokuto Denko Corporation.

(Experimental Results)

Figure 5C:
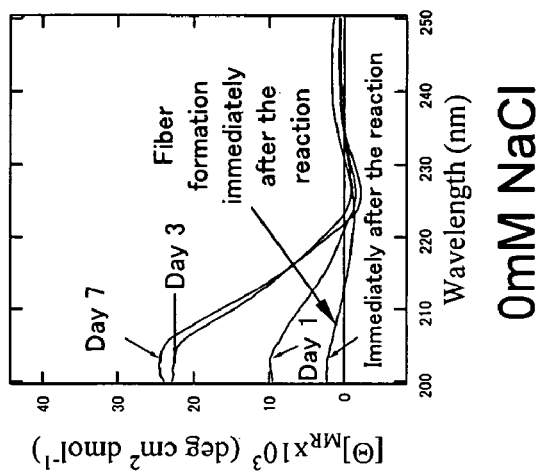
FIG. 5C is a graph showing CD measurement.
Figure 5B:
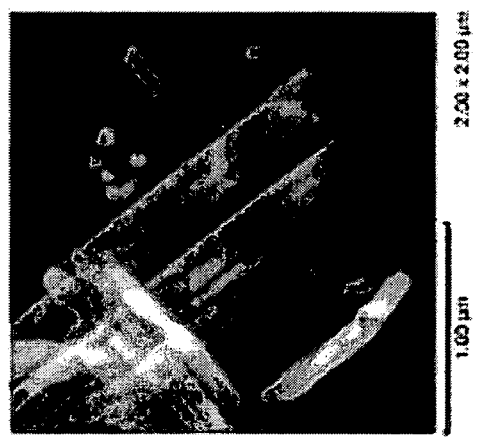
FIG. 5B is an AFM image of nanofibers.
Figure 5A:
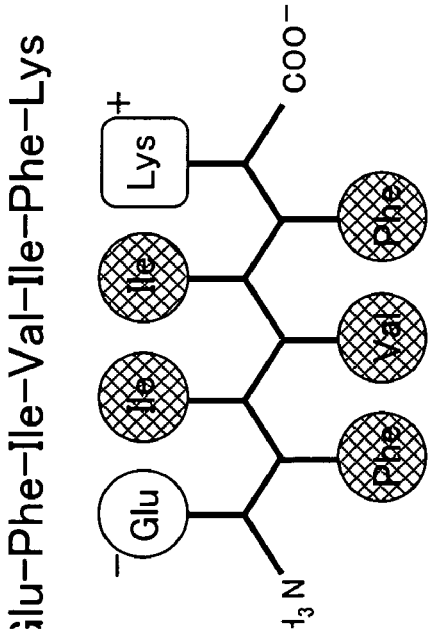
FIG. 5A is a schematic view of EK7aa.

1. Synthesis of Glu-Phe-Ile-Val-Ile-Phe-Lys (Abbreviated Expression: EK7aa) and Formation of Nanofiber Synthesis of EK7aa and reaction for forming nanofiber were carried out according to the above experimental method. FIG. 5A schematically illustrates EK7aa; FIG. 5B shows an AFM image of the nanofiber formed in 0 mM sodium chloride 7 days after formation of the fiber of EK7aa was initiated; and FIG. 5C shows a graph of CD measurement of EK7aa in 0 mM sodium chloride. As shown in FIG. 5A, EK7aa has an amino acid sequence including side chains of the amino acids at both ends having charge that negates the charge at both N, C-termini.

Presence of secondary structures (α-helix, β-sheet, random coil structures) of a protein can be verified by measuring CD. It has been known that CD spectrum of random coil structures generally has a negative minimum at around 200 nm, however, CD spectrum of this peptide immediately after initiation of the fiber formation exhibited a positive maximum at around 200 nm and a negative maximum value at around 225 nm (FIG. 5C). This is a spectrum characteristic in β-sheet structures, suggesting that the peptide immediately after initiation of the reaction already formed a β-sheet like structure through intermolecular interactions. Thereafter, CD spectrum altered with the course of time, and the alteration was not found after 3 days. This suggests that the nanofiber grew over 3 days.

Moreover, as shown in FIG. 5B, the AFM observation verified that the formed nanofiber has comparatively high linearity, with the height being 5 to 20 nm, and the length being 1 to 10 μm. Upon observation of each fiber in detail, it was elucidated that further fine fibers formed a fiber all together.

Congo red (CR) that is an organic compound is a dyeing reagent which has been classically used in detecting amyloid fibers. When CR bound to an amyloid fiber, green birefringence is verified by a polarizing microscope. This CR has been known to specifically bind to amyloid fibers, therefore, verification of the green birefringence will be one evidence showing that the aggregate is an amyloid fiber. Hence, the nanofiber formed from EK7aa was stained with CR, and observed with a polarizing microscope. Accordingly, green birefringence was verified. This suggests that the nanofiber formed from EK7aa is an amyloid fiber.

2. Biotinylation of Peptide Nanofiber

In order to ascertain that functional molecules are bound to a nanofiber formed from EK7aa, an experiment was conducted to allow biotin to which a functional group, i.e., sulf-N-hydroxy succinimide, was added similarly to the gold nanoparticle to bind to a nanofiber. Estimation of biotinylation efficiency showed a result of 0.077±0.001 mol/mol. Because two amino groups (at N-terminal and of the end of the side chain of the lysine residue) to which biotin can bind are present in the EK7aa sequence, it was ascertained that biotin was bound to the nanofiber at a rate of 1 molecule per about 13 molecules of EK7aa. This result suggests that any molecule can be added onto the surface of the peptide nanofiber through utilizing an amino group that is present on the peptide sequence.

3. Addition of Gold Particle to Peptide Nanofiber and Metal Plating

Furthermore, in order to impart conductive function to the nanofiber constituted from EK7aa, an experiment was conducted to allow gold nanoparticles to which a functional group, i.e., sulf-N-hydroxy succinimide, which is similar to one in biotinylation was added to bind to the nanofiber. FIG. 6A shows a light microscopic image of the nanofiber prior to addition of gold particles in a common blight filed, and FIG. 6B shows a light microscopic image obtained by observation with a differential interference filter. FIG. 7A shows a light microscopic image of the nanofiber to which gold particles were added in a common blight filed, FIG. 7B shows a light microscopic image obtained by observation with a differential interference filter, and FIG. 7C shows an AFM image.

When the nanofiber prior to the addition of gold nanoparticles was observed with a light microscope, to verify the presence was difficult in a common blight filed (FIG. 6A), but the presence of the fiber could be distinctly verified upon observation conducted with a differential interference filter (FIG. 6B). In addition, as shown in FIG. 5B, the fiber surface observed with AFM is found to be comparatively smooth. Thus, when the nanofiber to which gold nanoparticles were added was observed with a light microscopy, verification of the presence of the fiber was difficult in a common blight filed (FIG. 7A), but the presence of the fiber could be distinctly verified upon observation conducted with a differential interference filter (FIG. 7B), also in this case. Additionally, when the fiber was observed with AFM, as shown in FIG. 7C, the fiber surface was comparatively smooth, and the presence of the gold nanoparticle could not be distinctly verified, similarly to the case of the fiber prior to the addition of the gold nanoparticles. This event is believed to result from very small particle size of the used gold nanoparticle having a diameter of 1.4 nm.

Because possibility of the gold nanoparticles bound to the nanofiber not being in close contact with each other was supposed, particle size of the gold nanoparticle was enlarged by metal plating to narrow down the intervals among the metal particles.

(1) Silver Plating

Figure 8B:
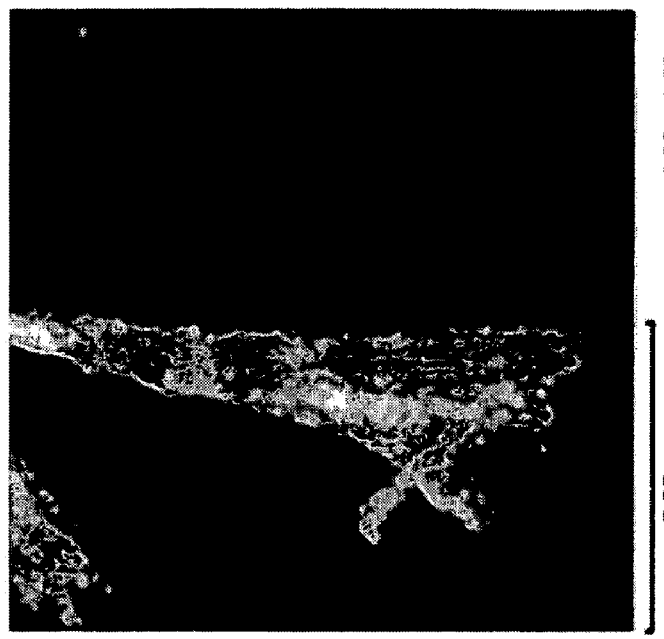
FIG. 8B shows an AFM image.
Figure 8A:
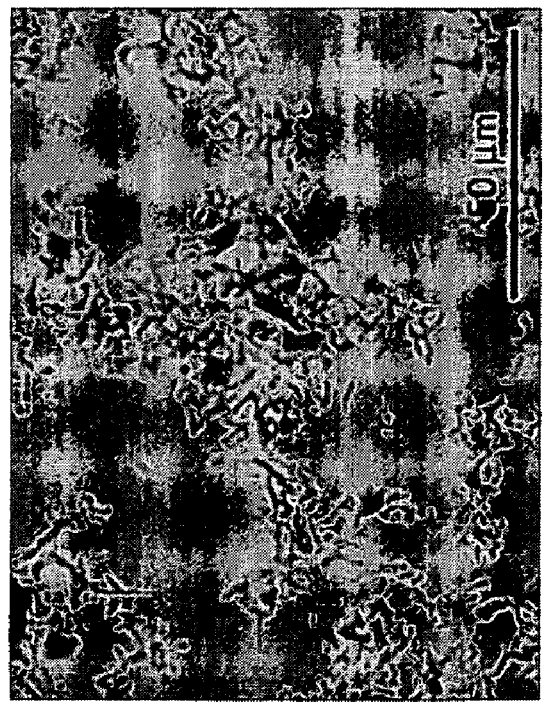
FIG. 8A shows a light microscopic image of a nanofiber of EK7aa subjected to silver plating.

Silver that is a metal species having the lowest resistivity among metals (resistivity=$1.6 \times 10^{-8}$ $\Omega$m (20° C.)) was deposited around the gold nanoparticles on the nanofiber. FIG. 8A shows a light microscopic image of a nanofiber in a common blight filed after subjecting to silver plating for 20 min, and FIG. 8B shows an AFM image. Heretofore, it was difficult to verify nanofibers in a common blight filed, however, when the silver plating was executed, nanofibers could be clearly verified even in a common blight field as shown in FIG. 8A. The nanofibers turned into black, indicating that silver was deposited around the fiber. Furthermore, upon AFM observation, as shown in FIG. 8B, it was ascertained that particles having a diameter of 5 to 20 nm were adhered on the nanofiber, greatly different from the surface of the fiber prior to subjecting to plating.

(2) Gold Plating

Figure 9B:
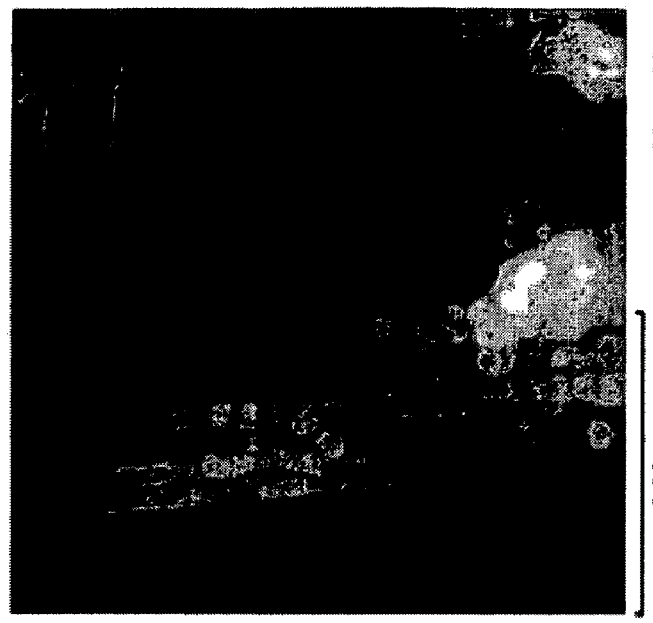
FIG. 9B shows an AFM image.
Figure 9A:
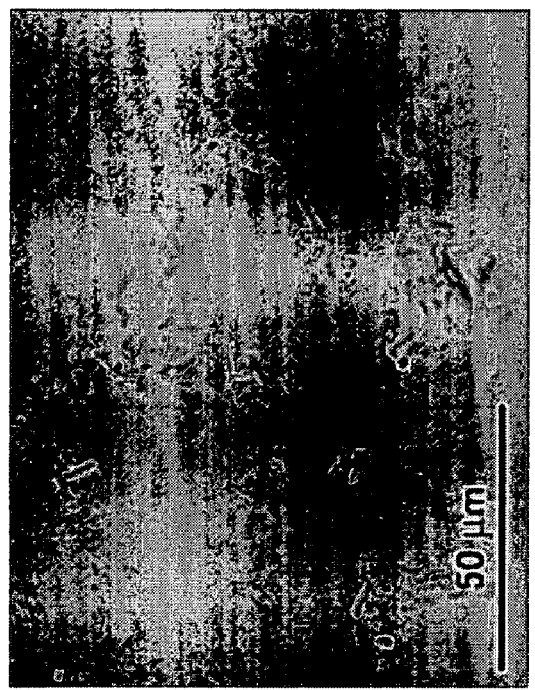
FIG. 9A shows a light microscopic image of a nanofiber of EK7aa subjected to gold plating.

Gold that is a metal species having the lowest resistivity among metals (resistivity=$2.4=10^{-8}$ $\Omega$m (20° C.)) was deposited around the gold nanoparticles on the nanofiber, in a similar manner to silver plating. Following the gold plating for 20 min, observation with a light microscopy in a common blight filed could verify the presence of chestnut-colored nanofiber, similarly to the silver plating (FIG. 9A). Observation of the surface was further conducted with AFM, and it was ascertained that particles having a diameter of 5 to 20 nm were adhered on the nanofiber (FIG. 9B).

The foregoing results suggest that the gold nanoparticles that could not be easily verified were surely added on the nanofiber, and that closer proximity of the metal particles was successfully achieved by way of the silver plating and gold plating. Moreover, nanofibers covered by the metal particles could be obtained without collapse of the fiber during the metal plating or during recovery of the fiber by centrifugation, suggesting that the nanofiber constituted from EK7aa is extremely structurally stable. It may be concluded that this physical property is advantageous also in light of industrial production in which a variety of processes for processing are assumed.

4. Measurement of Conductivity of Conductive Nanofiber

In order to ascertain whether the conductive nanofiber which was produced in practice has a conductive function, measurement of conductivity of the following 4 kinds of nanofibers was carried out:

(i) nanofiber constituted from EK7aa, (ii) EK7aa nanofiber to which gold nanoparticles were added, (iii) silver-plated EK7aa nanofiber, and (iv) gold-plated EK7aa nanofiber.

These 4 kinds of samples were placed on a comb-shaped electrode 21 (see, FIG. 4A), and measurements of direct-current electricity and measurement of impedance were carried out in the dried state (see, FIG. 4B), respectively. As a measurement of the standard, measurement of the electrode itself was also carried out without placing anything.

(1) Measurement of Direct-Current Electricity

Figure 10B:
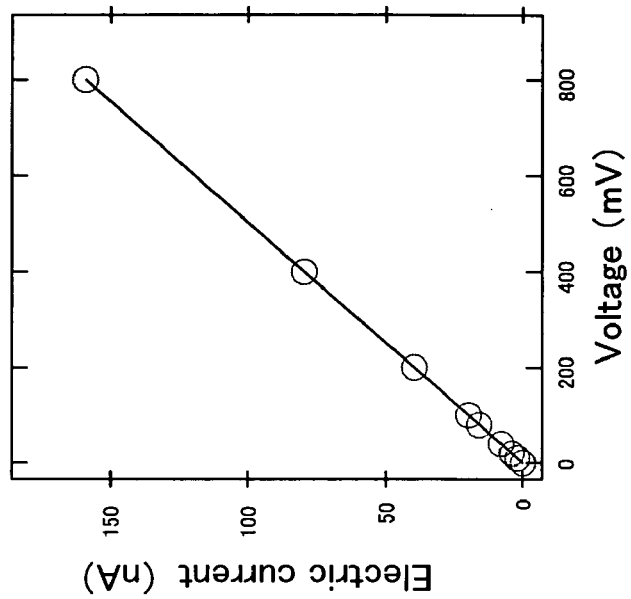
FIG. 10B shows the results of measurement of direct-current electricity of a nanofiber subjected to gold plating.
Figure 10A:
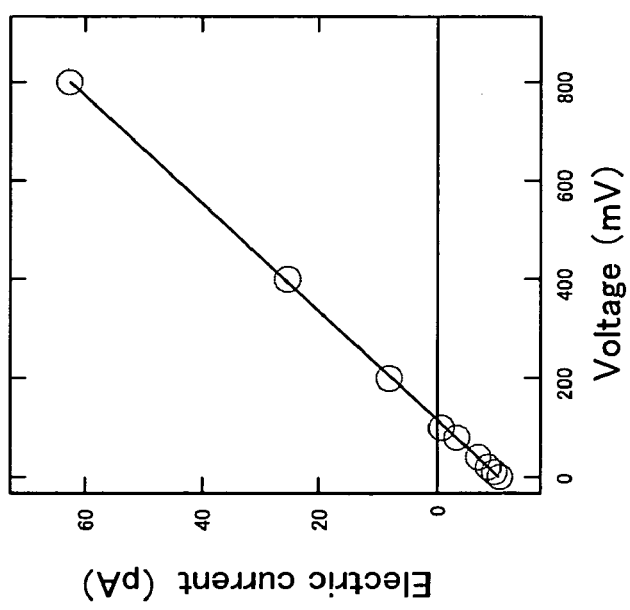
FIG. 10A shows the results of measurement of direct-current electricity of a nanofiber to which gold nanoparticles were added.

The samples (i) and (iii) were dead without any flow of electric current even though the power voltage was altered. Thus, ohmic resistance could not be determined. Although the sample (iii), i.e., the nanofiber subjected to silver plating, was expected to have the highest conductivity, it is speculated that silver was oxidized in the solution during the silver plating to turn into an insulator. The samples (ii) and (iv) were ascertained to live with a flow of electric current. Thus, ohmic resistance could be determined. FIG. 10A is a view illustrating voltage-electric current characteristic of the sample (ii); and FIG. 10B is a view illustrating voltage-electric current characteristic of the sample (iv). As shown in FIG. 10A, the sample (ii) had a resistance value of 10.9 G$\Omega$. Moreover, as shown in FIG. 10B, the sample (iv) had a resistance value of 5.03 M$\Omega$. Assuming that about 1000 pieces of the nanofiber were loaded on the tooth parts 26a, 27a of the electrode 21, the resistance value of each one nanofiber is revealed to be about 10.5 T$\Omega$ for the sample (ii), and about 5.03 G$\Omega$ for the sample (iv).

(2) Measurement of Impedance

Figure 11B:
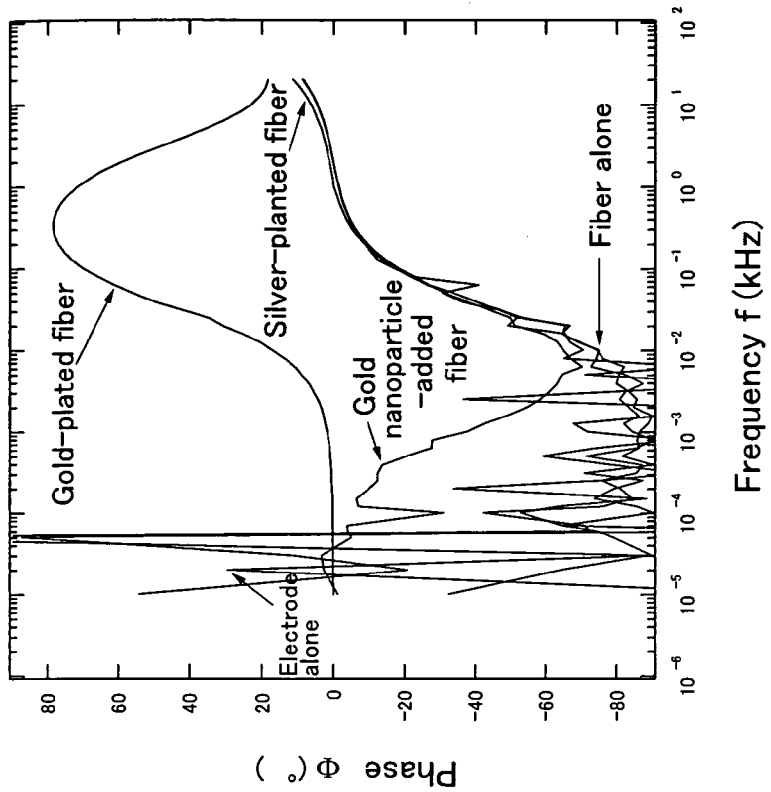
FIG. 11B shows the results of measurement of phase frequency.
Figure 11A:
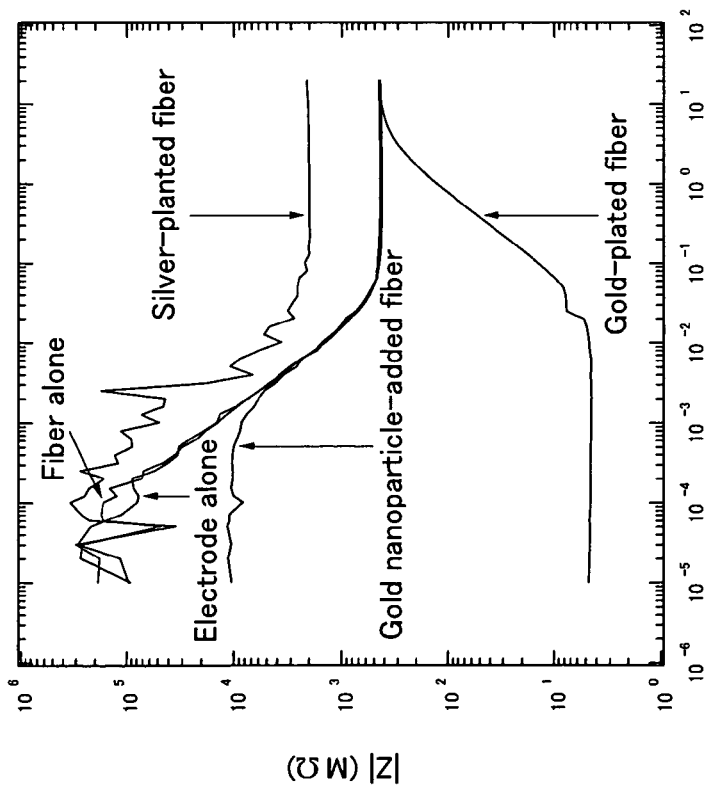
FIG. 11A shows the results of measurement of impedance of each nanofiber.
Figure 5C:
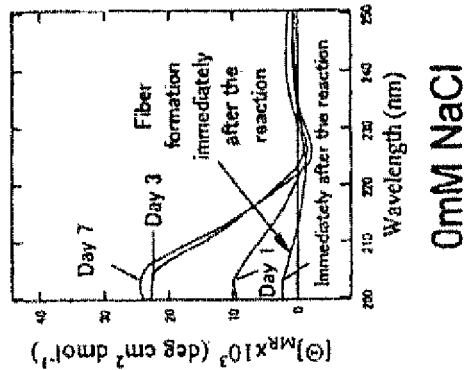
Figure 5B:
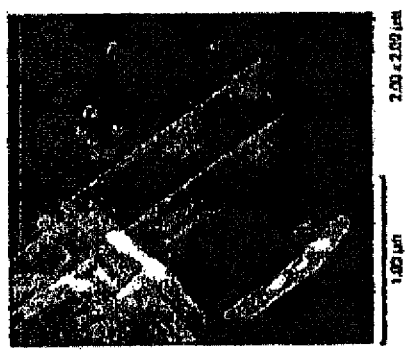
Figure 5A:
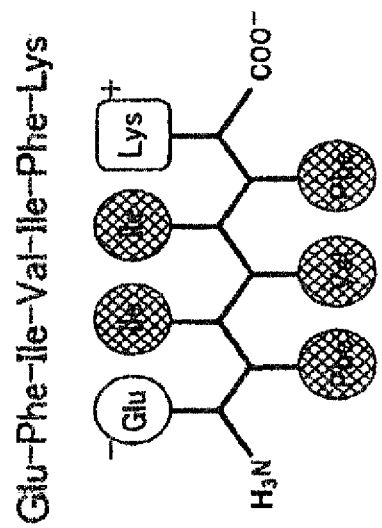

FIG. 11 shows results of measurement of impedance |Z| characteristic (FIG. 11A) and frequency characteristic with respect to φ (FIG. 11B) at 50 mV of the electrode alone and for each sample. It is revealed that the resistance values for electrode alone, the sample (i) and the sample (iii) at a lower frequency were approximately the same, about 100 GΩ, suggesting that they are almost an insulator. However, the resistance values of the samples (ii) and (iv) at the low frequency were revealed to be about 10 GΩ and about 5 MΩ, respectively. These values well agreed with the resistance values obtained by measurement of direct-current electricity.

The foregoing results suggest that electric current apparently flowed in cases of the nanofiber to which the gold nanoparticles were added, and the nanofiber subjected to gold plating, suggesting that the conductive function was successfully imparted. Moreover, when the sample (ii) was compared with the sample (iv), the sample (iv) exhibited improved conductivity about 1000 time greater than the sample (ii). This event is believed to result from increased particle size of the gold nanoparticles through gold plating, leading to close contact of the metal particles with each other.

In the above Examples, nanofiber-forming ability as well as capability to impart conductivity was verified only on EK7aa. In connection with a part of other peptide set out in SEQ ID NO: 1 according to the present invention, nanofiber-forming ability was ascertained in Japanese Patent Application Nos. 2003-385670 and 2004-151698 filed by Tamura et. al., the member of the present inventors. Also, in connection with other peptides according to the present invention, the present inventors believe that nanofiber-forming ability can be accomplished on the basis of the findings described hereinabove according to the present invention. Furthermore, any peptide according to the present invention has an amino group. Therefore, it is believed that peptide nanofibers exhibiting conductivity can be formed through adding a conductive substance by the method described above.

Under circumstances in which development of even finer and large-scale electronic circuits has been necessitated, the conductive peptide nanofiber at the nanoscale level according to the present invention is very advantageous. Use of the conductive peptide nanofiber of the present invention enables achieving nanofibers having a thickness of 10 nm or less and having conductivity. Accordingly, formation of current-conducting routes is permitted with a scale in a matter of fraction of those enabled by current semiconductor process techniques.

What is claimed is:

1. A conductive peptide nanofiber which comprises a nanofiber formed
    though a manner of self assembly of a peptide that has a nanofiber-forming ability and consists of the amino acid sequence SEQ ID NO: 2 and a conductive substance added thereto, wherein,
  said conductive substance is being added to an amino group of said peptide.

2. The conductive peptide nanofiber according to claim 1 wherein said conductive substance is a gold particle.

3. The conductive peptide nanofiber according to claim 2 wherein said gold particle has a diameter of 1 nm or greater and 20 nm or less.

4. The conductive peptide nanofiber according to claim 2 wherein said gold particle is covered by a metal formed by allowing a metal ion to deposit, with the gold particle as a core.

5. The conductive peptide nanofiber according to claim 4 wherein said metal ion is a gold ion or a silver ion.

6. The conductive peptide nanofiber according to claim 1 wherein said conductive substance is added to an amino group of said peptide or said derivative via an amino group-reactive material.

7. A method of manufacturing a conductive peptide nanofiber comprising:
   (a) preparing a nanofiber formed through a manner of self-assembly of a peptide that has a nanofiber-forming ability and consists of the amino acid sequence SEQ ID NO: 2; and
   (b) adding a conductive substance to an amino group of said peptide following said step (a).

8. The method of manufacturing a conductive peptide nanofiber according to claim 7 wherein said conductive substance is a gold particle.

9. The method of manufacturing a conductive peptide nanofiber according to claim 8 which further comprises
   (c) allowing a metal ion to deposit using said gold particle as a core following said step (b).

* * * * *

UNITED STATES PATENT AND TRADEMARK OFFICE
CERTIFICATE OF CORRECTION

PATENT NO. : 7,449,445 B2
APPLICATION NO. : 11/252719
DATED : November 11, 2008
INVENTOR(S) : Kentaro Onizuka et al.

It is certified that error appears in the above-identified patent and that said Letters Patent is hereby corrected as shown below:

IN THE DRAWINGS:

Please replace the Sheet 5 of 11 containing Fig. 5A with the drawing sheet attached.

In Column 14, Line 54 (Claim 1), change "is being added" to --is added--;

In Column 15, Line 3 (Claim 6), change "said peptide or said derivative" to --said peptide--; and In Column 15, Line 9 (Claim 7), change "SEQ 1ID" to --SEQ ID--.

Signed and Sealed this

Twelfth Day of January, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa is an arbitrary amino acid residue
<220> FEATURE:
<221> NAME/KEY: MISC_FEATURE
<222> LOCATION: (7)..(7)
<223> OTHER INFORMATION: Xaa is an arbitrary amino acid residue

<400> SEQUENCE: 1

Xaa Phe Ile Val Ile Phe Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Chemically synthesized

<400> SEQUENCE: 2

Glu Phe Ile Val Ile Phe Lys
1               5
```